United States Patent [19]

Cook et al.

[11] Patent Number: 4,643,717

[45] Date of Patent: Feb. 17, 1987

[54] ASPIRATION FITTING ADAPTOR

[75] Inventors: Kenneth P. Cook, Whitpain Township, Montgomery County; Robert M. Bross, Ivyland, both of Pa.

[73] Assignee: Site Microsurgical Systems, Inc., Horsham, Pa.

[21] Appl. No.: 776,260

[22] Filed: Sep. 16, 1985

[51] Int. Cl.[4] .............................................. A61B 17/20
[52] U.S. Cl. ........................................ 604/22; 604/48; 128/305
[58] Field of Search ..................... 604/22, 48; 433/86, 433/118, 119; 285/25, 28, 133 R; 128/24 A, 305, 303 C

[56] References Cited

U.S. PATENT DOCUMENTS 3,589,363 6/1971 Banko et al. .......................... 604/22
3,693,613 9/1972 Kelman ................................. 604/22
4,167,943 9/1979 Banko ................................. 128/305

Primary Examiner—C. Fred Rosenbaum
Assistant Examiner—J. L. Kruter
Attorney, Agent, or Firm—Jason Lipow

[57] ABSTRACT

The disposable adaptor to permit aspiration and/or irrigation fluid to pass through an ultrasonic surgical instrument without permitting leakage of the fluid from or into the interior of the instrument. The adaptor includes a generally annular housing defining a lumen for receiving the horn of the ultrasonic instrument and having inner seals forming a seal between the confronting surface of the adaptor and horn for prohibiting leakage along the exterior wall of the horn and an outer seal for forming a tight seal between the confronting surface of the adaptor and the instrument shroud for prohibiting leakage along the exterior surface of the adaptor. The adaptor includes a flange at its distal end with a circumferential groove extending partially about the adaptor and cooperating with a mating projection on the distal end of the instrument shroud to provide rotational orientation for the adaptor with respect to the shroud.

12 Claims, 6 Drawing Figures

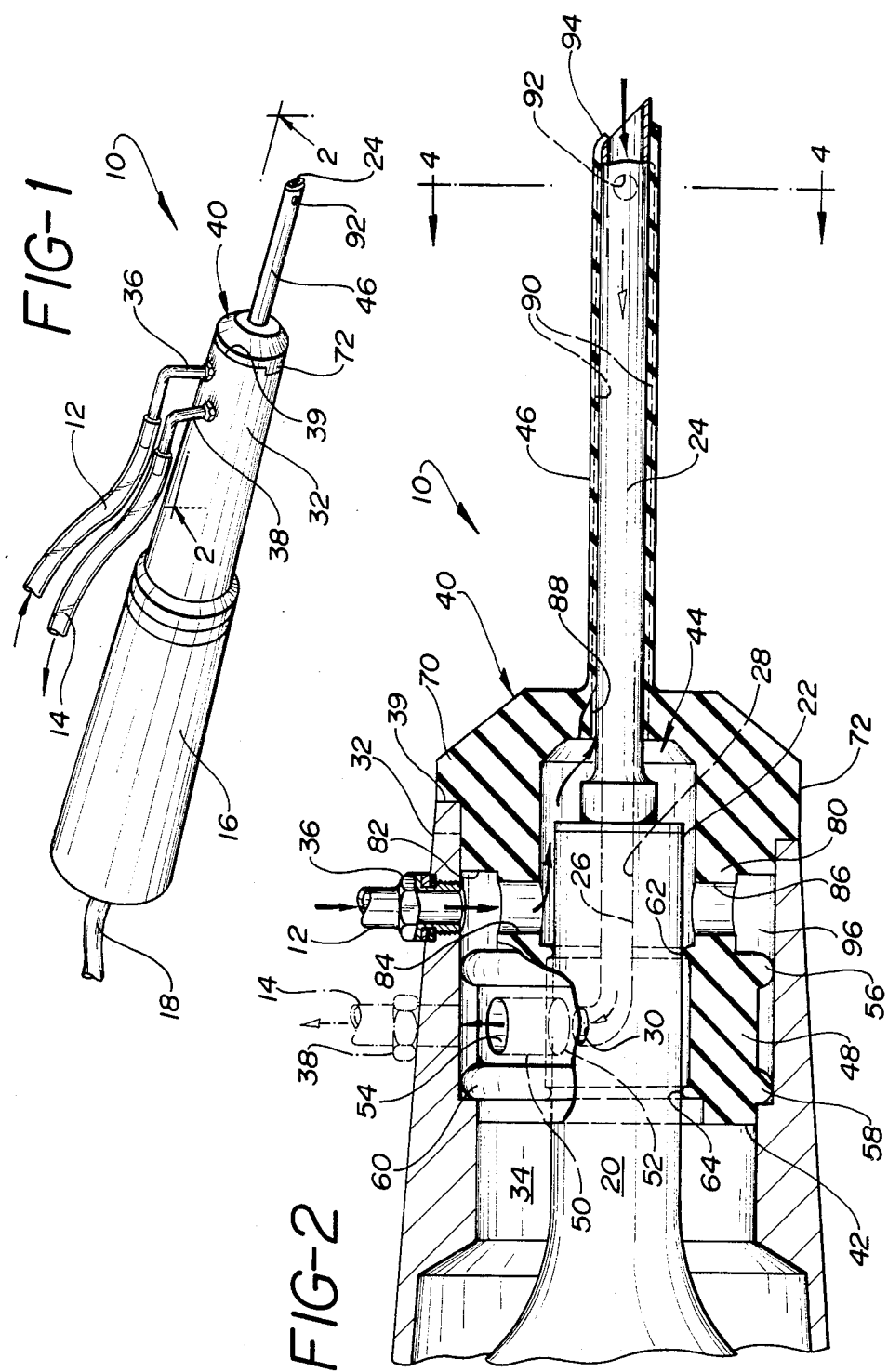

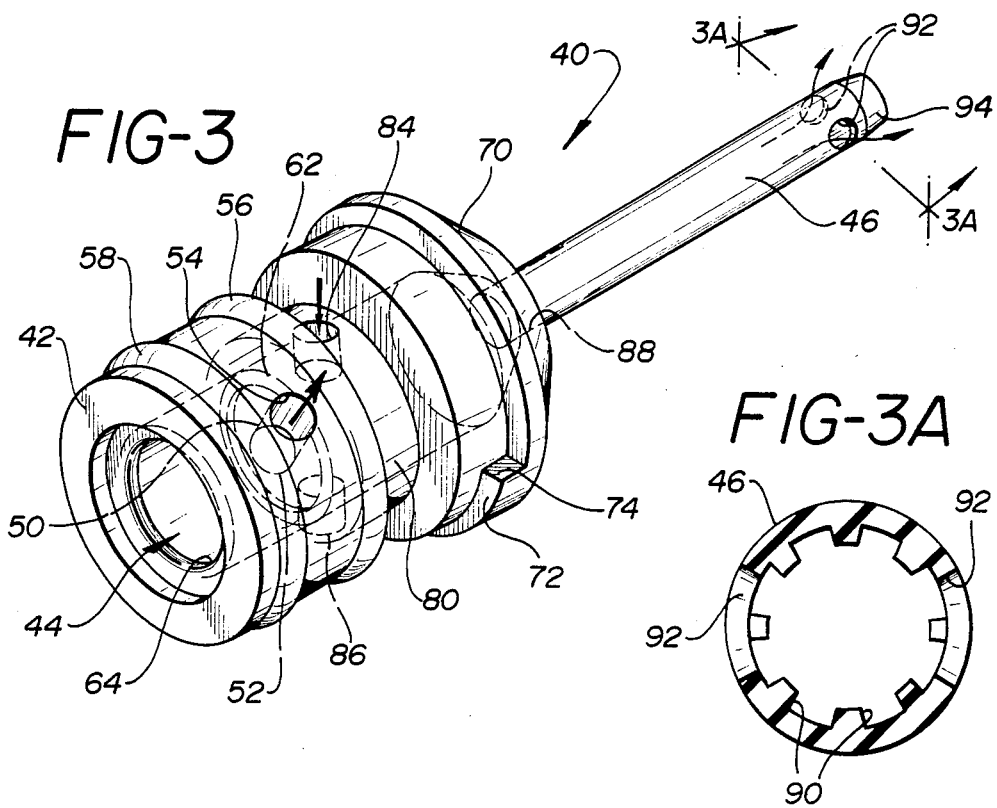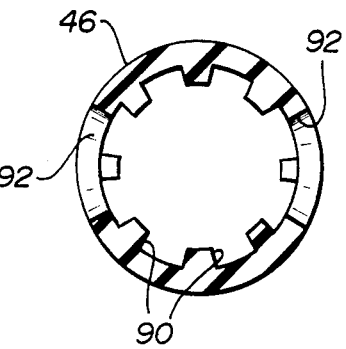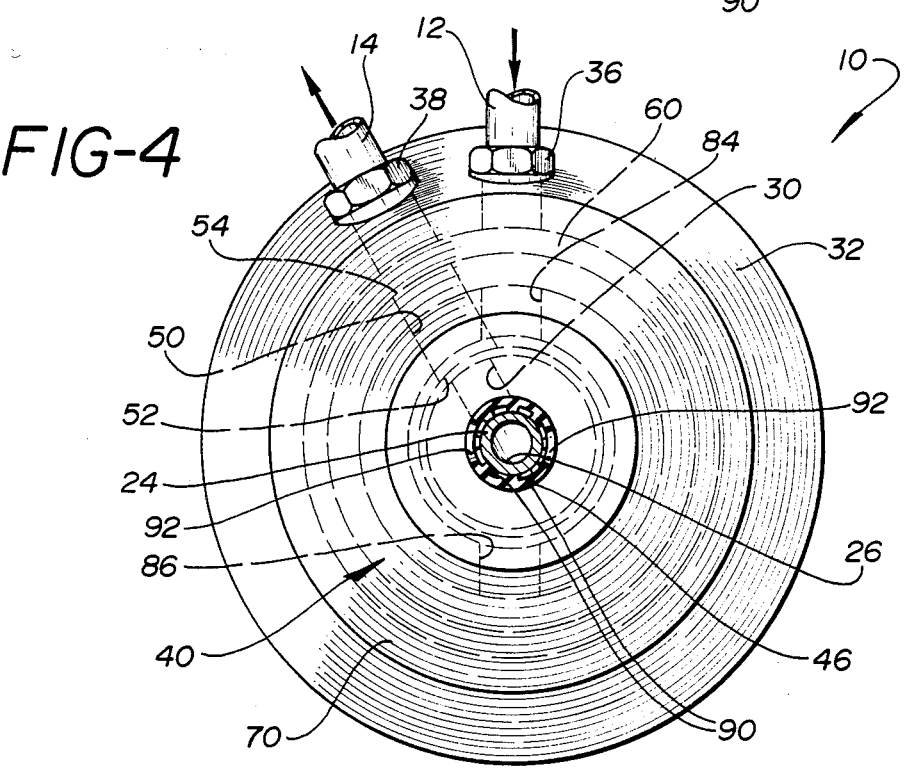

ASPIRATION FITTING ADAPTOR

FIELD OF THE INVENTION

The present invention relates to an adaptor fitting to be used with a half frequency surgical instrument for permitting aspiration and/or irrigation through the surgical instrument without fluid leakage.

BACKGROUND OF THE INVENTION

It is now commonly accepted that the vision impairing disease known as cataracts can be alleviate by surgically replacing the natural lens of the eye with an artificial intraocular lens. The condition of cataracts is characterized by the clouding of the natural lens of the eye so that the amount of light which reaches the retina is substantially reduced or completely eliminated.

The anatomy of the eye 1 is shown schematically in FIG. 5. The cornea 2 forms the front surface of eye 1 and connects with the ciliary muscle 3, from which the iris 4 extends. Iris 4 divides the front portion of eye 1 into the anterior chamber 5, between iris 4 and cornea 2, and a posterior chamber 6 behind iris 4. The capsular bag 7 in which the natural lens of the eye is encased is supported from ciliary muscle 3 by suspensory ligaments 8, called zonules. Pupil 9 is the aperture at the center of iris 4 through which light passes to posterior chamber 6 and to the back of the eye (not shown).

It is possible to remove a cataract len by cryogenic, mechanical or ultrasonic procedures.

The cryogenic techniques uses an insulated probe to freeze the lens into a solid mass to permit the frozen mass to be gripped and removed as a complete structure from capsular bag 7.

Mechanical means for removing the lens are shown for example in U.S. Pat. No. 4,002,169 where a small surgical tool is introduced into the eye by inserting a specially constructed hollow needle into the eye behind a rotary augering tool journaled in the hollow needle. Surgical procedures may then be performed with the rotary tool or with different tools inserted through the needle cannula to remove unwanted tissue such as cataracts. A rotary masticating tool may be introduced through the hollow needle. The unwanted tissue can then be masticated or liquified and then withdrawn through the needle bore following removal of the masticating tool. Similarly fluids may be injected into the body and withdrawn from the body through the hollow needle.

Ultrasonic removal of the cataract can be accomplished by the instrument and procedure shown, for example, in U.S. Pat. No. 3,589,363. That apparatus includes a casing in which is mounted a vibratory assembly for converting electrical energy into a high frequency mechanical vibrations which are used to break apart the unwanted cataract.

A transducer is located inside the casing and is connected to a acoustic impedence transformer or horn which has a relatively massive input section, a slender output section and a tapered transition section. The geometry of the horn can be designed to achieve the desired sonic wave form. A tip, usually a hollow cannula, can be attached to the distal end of the horn.

There are passages through the instrument for introducing (irrigating) treatment fluid to the region where the vibrations are applied to the eye and other passage for carrying away (aspirating) a slurry of unwanted material and treatment fluid from the eye.

The fluid lines cannot be directly attached to the vibrator assembly since that could dampen the vibration and cause loss of efficiency. In order to aspirate fluid through the ultrasonic instrument, aspiration holes are drilled through the casing and the horn. A chamber is created between the casing and the horn by placing flexible "O" rings around the horn and against the casing on either side of the aspiration holes. The aspiration line enters the chamber to provide negative pressure which is transmitted through the horn and the attached cannula to the operative site. Additional "O" rings may be used to establish separate irrigation passages.

Although present ultrasonic aspirators work satisfactorily, the use of "O" rings creates a maintenance problem. It would be desirable to have a ultrasonic device for emulsifying unwanted tissue, which would eliminate the need for "O" rings but would still maintain fluid passages without leakage for irrigation and/or separate aspiration.

SUMMARY OF THE INVENTION

The present invention provides an adaptor fitting which permits fluid to be aspirated through a high frequency phaco emulsifying surgical instrument. The adaptor has a generally annular housing defining a lumen into which the proximal end of which the horn of the transducer may be received and through the distal end of which the cannula attached to the distal end of the horn may protrude. A bore extends through the annular wall of the housing and may be aligned with an aspiration port in the instrument. The inner wall of the annular housing includes seals to prevent aspirated fluid from leaking along the interior of the lumen. The outer wall of the annular housing also includes seals for preventing aspirating fluid from leaking along the outer wall of the adaptor. There are cooperating projections and recesses on the distal end of instrument and on the adaptor to control the rotational alignment of the adaptor with respect to the instrument so that the bore through the adaptor wall will be aligned with the aspiration ports through the instrument.

The seals on the adaptor can include integral ribs extending circumferentially around the inner wall of the annular housing of the adaptor and similar ribs extending circumferentially around the outer wall of the annular housing of the adaptor.

The distal portion of the adaptor can include a radially extending flange extending outwardly beyond the surrounding side wall of the housing and having a proximally facing surface and a circumferential groove extending part way around the proximally facing surface of this flange. The instrument will have a cooperating projection extending from the distal end of the instrument to mate with this circumferential groove in the adaptor to control the rotational position of the adaptor with respect to the instrument.

Alternatively, the adaptor can also include an intermediate portion in the adaptor housing with a recess in the outer wall of the intermediate section and at least one irrigation bore through the recess to provide fluid communication with the lumen of the adaptor. Seals are provided on the outer surrounding wall of the housing distally of the intermediate portion to form a seal with the confronting surface of the instruments structure.

A generally annular sleeve may extend distally from the distal portion of the adaptor housing and define a lumen in fluid communication with the lumen of the adaptor. A plurality of axially extending ribs which project inwardly from the interior wall of the sleeve to provide support and a certain stiffness for the sleeve. Although the adaptor is usually provided with the sleeve integrally formed on the distal end of the adaptor, the sleeve may be cut off if it is not needed.

In this Application the word distal will be used to describe positions closer to the operative end of the instrument near the operative site and the word proximal will be used to describe portions of the apparatus farther away from the operative site.

These and other features and advantages of the present invention will become more apparent when taken in conjunction with the following detailed description of the preferred embodiment and the following drawings.

BRIEF DESCRIPTION OF THE DRAWINGS

FIG. 1 shows a perspective view of the ultrasonic irrigation/aspiration tool with which the adaptor fitting of the present invention is used;

FIG. 2 shows a detailed cross-sectional view of the adaptor of the present invention inserted in place on the ultrasonic apparatus and taken along lines 2—2 in FIG. 1;

FIG. 3 shows a perspective view of the adaptor of the present invention;

FIG. 4 shows an end view of the adaptor of FIG. 2 taken along lines 4—4 in FIG. 2; and, FIG. 5 shows a schematic representation of the anatomy of the eye with an ultrasonic aspirating instrument inserted into the eye in a position to remove a cataract.

DESCRIPTION OF THE PREFERRED EMBODIMENTS

Figure 5:
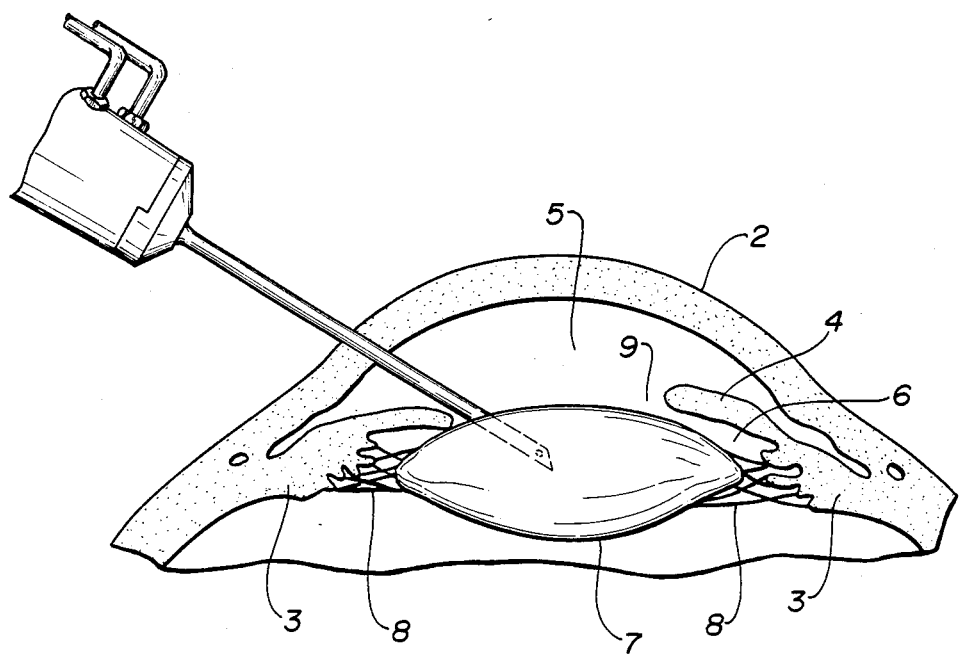

Referring now to FIG. 1 there is shown an ultrasonic surgical instrument 10 having an irrigation line 12 for introducing fluid into the instrument and ultimately to the operative site, and aspiration line 14 for removing aspiration fluid from the operative site through the instrument. The instrument includes a body portion 16 for housing an ultrasonic transducer (not shown). Power cord 18 is used to deliver electrical energy to the transducer inside body portion 16.

Referring now to FIG. 2, there is shown a horn portion 20 of an ultrasonic transformer for converting the mechanical vibrations developed by the transducer inside body portion 16 to vibrations of the desired wave form. The distal portion 22 of horn 20 includes a fitting (not shown) for rigidly affixing a hollow cannula 24 to distal end 22 for delivering ultrasonic vibrations of the desired wave form to the operative site. A passage 26 extends through horn 20 with a distal end 28 in fluid communication with hollow cannula 24 and proximal end 30 exiting through the side wall of horn 20.

Still referring to FIG. 2, there is shown an annular shroud portion 32 of instrument 10 extending around the distal end of horn 20 and spaced radially apart from horn 20 to provide an annular space 34 between shroud 32 and horn 20.

Irrigation line 12 connects to fitting 36 through shroud 32 to provide fluid communication with space 34. Aspiration line 14 connects to fitting 38 through shroud 32 to provide fluid communication with space 34. Referring now to FIGS. 1 and 4, it can be seen that aspiration port 38 is located proximally of irrigation port 36 and is spaced circumferentially away from irrigation port 36 a small amount of about 10°.

Referring now to FIG. 1, adaptor 40 is shown inserted into the distal end of instrument 10.

Referring now to FIG. 3, it can be seen that adaptor 40 includes a generally annular housing 42 defining a lumen 44. A generally cylindircal sleeve 46 projects from the distal end of adaptor 40.

The detailed structure of adaptor 40 will now be explained in conjunction with FIG. 2. Adaptor 40 includes a proximal portion of 48 having a bore 50 extending generally radially through the annular wall of housing 42 and defining an inner port 52 and an outer port 54. Outer port 54 is aligned generally with aspiration fitting 38. Inner port 52 is aligned generally with the proximal end 30 of passage 26 through horn 20.

Seals 56 and 58 are formed of generally annular ribs on the outer wall of annular housing 42 and spaced axially apart with seal 56 being placed distally of aspiration bore 50 and seal 58 being place proximally of aspiration bore 50. Seals 56 and 58 seal firmly against the confronting inside wall of shroud 32 to provide a liquid tight seal to prevent aspiration fluid from leaking along the outer wall of adaptor 40. Seal 58 rests against a step 60 on the inside wall of shroud 32 which step 60 provides a stop against which adaptor 40 will bottom when inserted into shroud 32.

Seals 62 and 64 on the inner wall of annular housing 42 project radially inward into tight sealing engagement with horn 20. Seals 62 and 64 are annular ribs integrally formed on the inner wall of housing 42 and are spaced axially apart with seals 64 being located proximally of bore 50 and seal 62 being located distally of bore 50.

It will be appreciated that if suction is applied to aspiration line 14 fluid may be removed from the operative site through hollow cannula 24, passage 26, bore 50 and fitting 38 in shroud 32 to provide a liquid tight fluid passage which will prevent leakage along the outer wall of adaptor 40 or along the wall of horn 20.

Still referring to FIG. 2 it can be seen that the distal end 70 of adaptor 40 includes a flange 72 extending radially outwardly and completely circumferentially about adaptor 40. A groove 74 extends distally into flange 72 and circumferentially part way about flange 72. A corresponding projection 39 extends distally from the distal end of shroud 32 and mates with groove 74 of flange 72 to provide rotational orientation of adaptor 40 with respect to shroud 32 and particularly aspiration fitting 38 of shroud 32 and aspiration bore 50 of adaptor 40. It is desirable to have aspiration bore 50 of aligned with passage 26 of horn 20 and fitting 38 of aspiration line 14 so that particles of tissue aspirated through the apparatus will be less likely to be trapped between adaptor 40 and the interior wall of shroud 32.

In the preferred embodiment adaptor 40 is provided with a means for introducing irrigation fluid into the operative site through the instrument. Adaptor 40 includes an intermediate section 80 located distally of outer seal 56 and having a recess 82 extending radially inwardly and extending circumferentially about the intermediate portion 80. A bore 84 extends from the bottom of recess 82 through the wall of housing 42 to provide fluid communication with lumen 44 proximally of inner seal 62.

Alternatively additional bores 86 may be included in intermediate portion 80.

Still referring to FIG. 2, it can be seen that cannula 24 projects through a bore 88 in the distal end of adaptor 40. An annular sleeve 46 extends distally about the periphery of bore 88. Ribs 90 extend axially along the interior wall of sleeve 46 and project radially inward a short distance to add stiffness to sleeve 46 and to provide fluid passages for irrigation fluid to flow between ribs 90 along the outside wall of cannula 24. Ribs 90 are shown dashed in FIG. 2 and in cross section in FIG. 4.

Close to the distal end of sleeve 46 there are provided a plurality of bores 92 extending radially through the wall of sleeve 46 to permit irrigation fluid to exit from the space between the outside wall of cannula 24 and the inside wall of sleeve 46 to the operative site.

From FIG. 1 it can be seen that irrigation fluid can enter instrument 10 through irrigation line 12, through fitting 36, into space 34, through bore 84, into lumem 44 along the exterior of cannula 24 and out through bores 92 into the operative site.

An inwardly extending bevel 94 extends circumferentially around the distal tip of sleeve 46.

Bevel 94 provides a tight seal between sleeve 46 and the exterior wall of cannula 24 to prohibit aspiration fluid from entering between sleeve 46 and cannula 24 and to inhibit the flow of irrigation fluid axially out the distal end of cannula 24 where it could be aspirated right back into hollow cannula 24 without providing the necessary irrigation function.

It can be seen from FIG. 2 that a chamber 96 is formed between the confronting surfaces of intermediate section 80, seal 56, the interior wall of shroud 32 and flange 72 through which irrigation fluid can circulate and then pass through bores 84 and 86 through lumen 44 and through the space provided by ribs 90 between the interior wall of sleeve 46 and the outside wall of cannula 24. In those instances where irrigation is not desired sleeve 46 can be cut off from adaptor 40.

It will be appreciated that the present adaptor provides a convenient fitting for permitting irrigation and/or aspiration fluid to circulate through an ultrasonic surgical instrument without permitting the irrigation and/or aspiration fluid to mix with one another or to leak from or into the interior or the instrument.

Irrigation line 12 and aspiration line 14 are disposable plastic tubes. Adaptor 40 is preferably disposable. Disposable adaptor 40 provides a convenient fitting which eliminates the assembly and cleaning problems of prior ultrasonic surgical instruments caused particularly by the use of "O" rings in their construction.

The present invention has been described in conjunction with preferred embodiments. Those skilled in the art will appreciate that many modifications and changes may be made to the preferred embodiments without departing from the present invention. It is therefore, not intended to limit the present invention except to set forth in the following claims.

We claim:

1. An adaptor for a surgical device, said surgical device comprising: an elongated instrument having a proximal end and a distal end; a probe extending axially from said distal end; and a shroud surrounding, but spaced away from, the distal portion of said instrument;
   said adaptor having means adapted for insertion into said device between said shroud and the distal portion of said instrument, and permitting fluid to flow through said device; said adaptor comprising:
   a generally annular housing wall having an outer wall surface and an inner wall surface, said inner wall surface surrounding a lumen, said lumen extending longitudinally through said adaptor for receiving the distal portion of the instrument with the probe extending distally from the adaptor;
   a fluid bore extending through the housing wall and terminating at an inner port in the inner wall surface and an
   outer port in the outer wall surface;
   said inner port adapted for alignment with a first fluid port in said instrument and said outer port adapted for alignment with a first fluid port in said shroud;
   adaptor alignment means on said adaptor for cooperating with device alignment means on said device for so aligning said inner and outer ports with said first and second fluid ports;
   inner sealing means depending from said inner wall surface for fluidly isolating said inner port and for forming a seal with the confronting surface of the instrument and prohibiting leakage of fluid along said lumen; and outer sealing means projecting from said outer wall surface for fluidly isolating said outer port and for forming a seal with a confronting surface of said shroud and prohibiting leakage of fluid along said outer wall surface of said adaptor.

2. The adaptor of claim 1 wherein said inner sealing means comprise at least two ribs formed integrally with said annular housing wall, said ribs extending circumferentially about said inner wall surface, spaced axially apart there along, and extending radially inward.

3. The adaptor of claim 1 wherein said outer sealing means comprise at least two ribs formed integrally with said annular housing wall, said ribs extending circumferentially about said outer wall surface, spaced axially apart there along, and extending radially outward.

4. The adaptor of claim 1 wherein said adaptor alignment means comprise:
   a radially extending flange on the distal portion of said adaptor extending radially outward beyond the outer wall surface of said housing wall, said flange having a proximally facing surface; a circumferential groove extending partway about the proximally facing surface of said flange and adapted to cooperate with device alignment means on said device which device alignment means comprise a corresponding projection extending from the distal end of said device to rotationally position said adaptor in its desired position with respect to said device.

5. The adaptor of claim 1 further including means to permit a second fluid to flow through said device comprising:
   providing, in a section of said outer wall surface of said housing wall spaced away from said fluid bore, a recessed portion extending circumferentially about the outer wall surface;
   a second fluid bore extending through said recessed portion to provide fluid communication to said lumen through said housing wall; additional sealing means on said outer wall surface of said housing wall for forming a seal with the confronting surfaces of the shroud.

6. The adaptor of claim 5 further including a generally annular sleeve having a surrounding side wall, said sleeve extending distally from the distal portion of said adaptor housing wall and defining a second lumen in flow communication with the lumen of said adaptor.

7. The adaptor of claim 6 further including a plurality of axially extending ribs extending radially inward into said second lumen.

8. The adaptor of claim 6 wherein said sleeve comprises a distal tip including a beveled portion beveled radially inward and further includes at least one radially extending opening through the side wall of said sleeve to permit fluid communication out of said second lumen.

9. The adaptor of claim 5 wherein said second fluid bore is spaced circumferentially from said fluid bore.

10. The adaptor of claim 5 wherein said recessed portion includes at least two bores there through spaced on opposite portions of said recessed portion.

11. An adaptor for permitting a first fluid to be aspirated through a high-frequency, phaco emulsifier surgical instrument without permitting said fluid to leak from said instrument;
said instrument having:
a handle having a proximal portion and a distal portion and a surrounding side wall;
transducer means housed within said handle for generating a high-frequency sonic vibration;
a vibration horn operatively connected to said transducer means;
a vibrating tip including a hollow cannula operatively connected to said horn; and,
said handle including a shroud generally surrounding said horn in spaced-apart relationship and defining an annular space about said horn in the vicinity of the distal portion of said instrument;
said horn having a passage therethrough providing fluid communication between said hollow cannula and said annular space through which fluid may be aspirated;
said shroud having an aspirating port therethrough for providing fluid communication through said shroud to said annular space;
said adaptor comprising:
a generally annular housing adapted to fit in the annular space defined between said horn and said shroud at the distal tip of said instrument, said annular housing having a proximal end, a distal end, a surrounding outer side wall and a surrounding inner wall defining a lumen extending axially from said proximal and distally into said housing, the distal end of said housing including a bore extending axially therethrough and in fluid communication with said lumen;
said annular housing adapted to fit in said generally annular space at the distal end of said instrument about the distal tip of said horn with said cannula projecting through said adapter housing lumen and said distal end bore and extending distally from said adapter;
at least one aspiration bore extending through a proximal portion of said adaptor housing wall and having an inner port in said inner wall of said adaptor housing and an outer port in the surrounding outer wall of said adaptor housing, the inner port of said aspiration bore aligned for fluid communication with said aspiration port of said horn and said outer port of said aspiration bore aligned of fluid communication with said shroud aspiration port to provide fluid communication for aspirating fluid through the cannula, said passage in said horn, said adapter housing aspiration bore and said shroud aspiration port;
sealing means disposed about said adapter housing interior wall port for forming a seal with the confronting surface of said horn;
sealing means about the aspiration port in the outer sidewall of said adaptor housing for forming a seal with the confronting interior surface of said instrument shroud; and
cooperative means on the distal portions of said instrument and said adaptor respectively for rotationally aligning said aspiration bore with said first and second aspiration ports of said instrument.

12. The adaptor of claim 11 further including means to permit a second fluid to be irrigated through said instrument without permitting said aspiration or said irrigation fluid to mix with one another or to leak from said instrument comprising:
an intermediate section of said generally annular housing disposed between the distal and proximal ends thereof;
a recessed portion in the outer wall of said intermediate section extending circumferentially thereabout;
at least one irrigation bore through the recessed portion to provide fluid communication to said lumen through said housing wall;
sealing means on the outer wall of said housing, distally of said intermediate portion for forming a seal with the confronting surface of said shroud; and
said shroud also having an irrigation port therethrough for providing fluid communication to said annular space, said irrigation port space axially from said aspiration port through said shroud.

* * * * *